US00PP20386P2

(12) United States Plant Patent
Lemon

(10) Patent No.: US PP20,386 P2
(45) Date of Patent: Oct. 6, 2009

(54) ***GERANIUM* PLANT NAMED 'OGLGER11010'**

(50) Latin Name: *Pelargonium×domesticum*
Varietal Denomination: Oglger11010

(75) Inventor: David Lemon, Lompoc, CA (US)

(73) Assignee: Ecke Geraniums, LLC, Encinitas, CA (US)

( * ) Notice: Subject to any disclaimer, the term of this patent is extended or adjusted under 35 U.S.C. 154(b) by 0 days.

(21) Appl. No.: 12/156,716

(22) Filed: Jun. 3, 2008

(51) Int. Cl.
*A01H 5/00* (2006.01)

(52) U.S. Cl. ..... Plt./331

(58) Field of Classification Search ..... Plt./331
See application file for complete search history.

*Primary Examiner*—Kent L Bell
(74) *Attorney, Agent, or Firm*—C. A. Whealy

(57) ABSTRACT

A new and distinct cultivar of Regal *Geranium* plant named 'Oglger11010', characterized by its upright, outwardly spreading and mounded plant habit; freely branching habit; freely flowering habit; early to mid-flowering habit; bright lilac and magenta-colored flowers; and good garden performance.

1 Drawing Sheet

Botanical designation: *Pelargonium×domesticum.*
Cultivar denomination: 'Oglger11010'.

BACKGROUND OF THE INVENTION

The present invention relates to a new and distinct cultivar of Regal *Geranium,* botanically known as *Pelargonium×domesticum*, and hereinafter referred to by the name 'Oglger11010'.

The new Regal *Geranium* is a product of a planned breeding program conducted by the Inventor in Lompoc, Calif. The objective of the breeding program is to create new freely-branching and early-flowering Regal *Geranium* cultivars with attractive and unique flower coloration.

The new Regal *Geranium* originated from a cross-pollination made by the Inventor in June, 2000 in Lompoc, Calif. of the *Pelargonium×domesticum* cultivar Prince, disclosed in U.S. Plant Pat. No. 8,090, as the female, or seed, parent with the *Pelargonium×domesticum* cultivar Partisan, not patented, as the male, or pollen, parent. The cultivar Oglger11010 was discovered and selected by the Inventor as a flowering plant from within the progeny of the stated cross-pollination in a controlled environment in Lompoc, Calif. in February, 2001.

Asexual reproduction of the new Regal *Geranium* by vegetative terminal cuttings in a controlled environment in Connellsville, Pa. since February, 2002, has shown that the unique features of this new Regal *Geranium* are stable and reproduced true to type in successive generations.

SUMMARY OF THE INVENTION

The cultivar Oglger11010 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Oglger11010'. These characteristics in combination distinguish 'Oglger11010' as a new and distinct cultivar of Regal *Geranium*:

1. Upright, outwardly spreading and mounded plant habit.
2. Freely branching habit.

3. Freely flowering habit.
4. Early to mid-flowering habit.
5. Bright lilac and magenta-colored flowers.
6. Good garden performance.

Plants of the new Regal *Geranium* differ primarily from plants of the female parent, the cultivar Prince, primarily in flower color as plants of the cultivar Prince have pink and white bi-colored flowers.

Plants of the new Regal *Geranium* differ primarily from plants of the male parent, the cultivar Partisan, primarily in flower color as plants of the cultivar Partisan have lilac-colored flowers. In addition, plants of the new Regal *Geranium* flower earlier than and are not as vigorous as plants of the cultivar Partisan.

Plants of the new Regal *Geranium* can be compared to plants of the *Pelargonium×domesticum* cultivar Elegance Lavender, disclosed in U.S. Plant Pat. No. 17,779. In side-by-side comparisons conducted in Connellsville, Pa., plants of the new Regal *Geranium* differed from plants of the cultivar Elegance Lavender in the following characteristics:

1. Plants of the new Regal *Geranium* were more compact than plants of the cultivar Elegance Lavender.
2. Plants of the new Regal *Geranium* and the cultivar Elegance Lavender differed in flower color as plants of the cultivar Elegance Lavender had lavender-colored flowers.

BRIEF DESCRIPTION OF THE PHOTOGRAPH

The accompanying colored photograph illustrates the overall appearance of the new Regal *Geranium*, showing the colors as true as it is reasonably possible to obtain in colored reproductions of this type. Colors in the photograph may differ slightly from the color values cited in the detailed botanical description which accurately describe the colors of the new Regal *Geranium*. The photograph comprises a side perspective view of a typical flowering plant of 'Oglger11010' grown in a container.

DETAILED BOTANICAL DESCRIPTION

The aforementioned photograph and following observations, measurements and values describe plants grown in Connellsville, Pa. in a glass-covered greenhouse during the summer and under conditions which closely approximate Regal *Geranium* commercial production. During the production of the plants, day temperatures ranged from 21° C. to 32° C., night temperatures ranged from 17° C. to 21° C. and light levels ranged from 2,500 lux to 3,000 foot-candles. Plants were about 14 weeks from planting when the photographs and the description were taken. In the detailed description, color references are made to The Royal Horticultural Society Colour Chart, 2001 Edition, except where general terms of ordinary dictionary significance are used.

Botanical classification: *Pelargonium×domesticum* cultivar Oglger11010.

Parentage:

*Female, or seed, parent.*—*Pelargonium×domesticum* cultivar Prince, disclosed in U.S. Plant Pat. No. 8,090.

Male or pollen parent.—*Pelargonium×domesticum* cultivar Partisan, not patented.

Propagation:

*Type.*—By vegetative terminal cuttings.

*Time to initiate roots, summer.*—About nine to ten days at temperatures of 20° C.

*Time to initiate roots, winter.*—About 13 to 14 days at temperatures of 18° C.

*Time to produce a rooted young plant, summer.*—About 17 to 20 days at temperatures of 20° C.

*Time to produce a rooted young plant, winter.*—About 21 to 24 days at temperatures of 18° C.

*Root description.*—Fine, fibrous; white in color.

*Rooting habit.*—Moderate branching; moderately dense.

Plant description:

*General appearance.*—Upright and outwardly spreading plant habit; uniformly mounded; densely foliated.

*Growth and branching habit.*—Moderately vigorous growth habit. Freely branching habit.

*Plant height, to top of foliar plane.*—About 15 cm.

*Plant height, to top of umbels.*—About 21 cm.

*Plant width:*—About 20 cm.

*Main stems.*—Length: About 11 cm. Diameter: About 9 mm. Internode length: About 3 mm to 5 mm. Texture: Moderately pubescent. Strength: Strong. Color: Slightly darker than 143A.

*Primary lateral branches.*—Length: About 6 cm to 8 cm. Diameter: About 5 mm to 10 mm. Internode length: About 1.5 cm to 2.4 cm. Texture: Moderately pubescent. Strength: Strong. Color: 144B.

Foliage description:

*Arrangement.*—Towards the base of the plant, opposite; towards the apex of the plant, alternate; simple.

*Length.*—About 3 cm to 6.5 cm.

*Width.*—About 4.5 cm to 9 cm.

*Shape.*—Reniform.

*Apex.*—Acute.

*Base.*—Truncate.

*Margin.*—Serrate, lobed.

*Venation pattern.*—Palmate.

*Texture, upper and lower surfaces.*—Pubescent; leathery.

*Color.*—Developing foliage, upper surface: 143A to 143B. Developing foliage, lower surface: 143C. Fully expanded foliage, upper surface: Slightly darker than 143A; venation, slightly darker than 143A. Fully expanded foliage, lower surface: 138B; venation, 144B. Zonation pattern: Not observed.

Petiole.—Length: About 3 cm to 5 cm. Diameter: About 2 mm to 3 mm. Texture, upper and lower surfaces: Smooth, glabrous. Color, upper and lower surfaces: Slightly darker than 143A.

Flower description:

*Flower arrangement.*—Rotate flowers arranged in rounded umbels arising from apical leaf axils. Umbels displayed above the foliage on strong peduncles. Flowers face upright to outward; flowers slightly cupped. Flowers not persistent. Flowers not fragrant.

*Quantity of flowers.*—Freely flowering habit; about four to five flowers per umbel and about two to three umbels per lateral branch.

*Flowering season.*—In Connellsville, Pa., flowering is continuous during the spring.

*Flower longevity.*—Individual flowers last about 30 days on the plant.

*Umbel height.*—About 5 cm to 6 cm.

*Umbel diameter.*—About 8 cm to 9 cm.

*Flower diameter.*—About 5.5 cm to 6.5 cm.

*Flower depth* (*height*).—About 2.5 cm to 3 cm.

*Petals.*—Quantity per flower: About five in a single whorl; two larger upper petals and three smaller lower petals. Length, upper petals: About 3.5 cm. Length, lower petals: About 2.5 cm. Width, upper petals: About 4 cm. Width, lower petals: About 2.5 cm. Shape, upper and lower petals: Roughly spatulate. Apex, upper and lower petals: Rounded. Base, upper and lower petals: Truncate. Margin, upper and lower petals: Entire; ruffled. Texture, upper and lower petals, upper and lower surfaces: Smooth, glabrous. Color: Upper petals, when opening and fully opened, upper surface: Close to 72B, overlain with close to 71C; towards the base, close to 155D; central blotch, close to N79C; venation, close to N79C. Lower petals, when opening and fully opened, upper surface: Initially 77C becoming closer to 72B with development overlain with close to 72B; towards the base, close to 155D; venation, 72B. Upper petals, when opening and fully opened, lower surface: Close to 155D; towards the apex, close to 77B to 77C; venation, close to 72B. Lower petals, when opening and fully opened, upper surface: Close to 155D; towards the apex, close to 77B to 77C; venation, similar to lamina.

*Petaloids.*—None observed.

Sepals.—Quantity per flower: Five, arranged in a single whorl. Length: About 1.8 cm to 2 cm. Width: About 5 mm. Shape: Lanceolate. Apex: Acute. Base: Attenuate. Margin: Entire. Color, upper and lower surfaces: Close to 144A.

*Peduncle* (*umbel stem*).—Length: About 5 cm. Diameter: About 2 mm. Strength: Strong. Texture: Pubescent. Color: 144A.

*Pedicel* (*individual flower stem*).—Length: About 1.5 cm. Diameter: About 1 mm. Strength: Moderately strong. Texture: Pubescent. Color: 144A; towards the sepals, overlain with 166A.

*Reproductive organs.*—Androecium: Stamen quantity per flower: About eight. Filament length: About 5 mm to 10 mm. Filament color: Close to 155D. Anther length: About 2 mm. Anther shape: Elongated oval. Anther color: N79C. Pollen amount: Moderate. Pollen color: N172D. Gynoecium: Pistil quantity per flower: One. Pistil length: About 1.2 cm to 1.8 cm. Stigma shape: Split into six parts. Stigma size: About 5 mm. Stigma color: 71A. Style length: About 1 cm. Style color: 71C. Ovary color: 144A.

*Seed.*—Seed development has not been observed.

Disease/pest resistance: Plants of the new Regal *Geranium* have not been observed to be resistant to pathogens and pests common to Regal *Geraniums.*

Garden performance: Plants of the new Regal *Geranium* have been observed to tolerate rain, wind, and temperatures ranging from about 1° C. to about 35° C. and have demonstrated good garden performance.

It is claimed:

1. A new and distinct Regal *Geranium* plant named 'Oglger11010,' as illustrated and described.

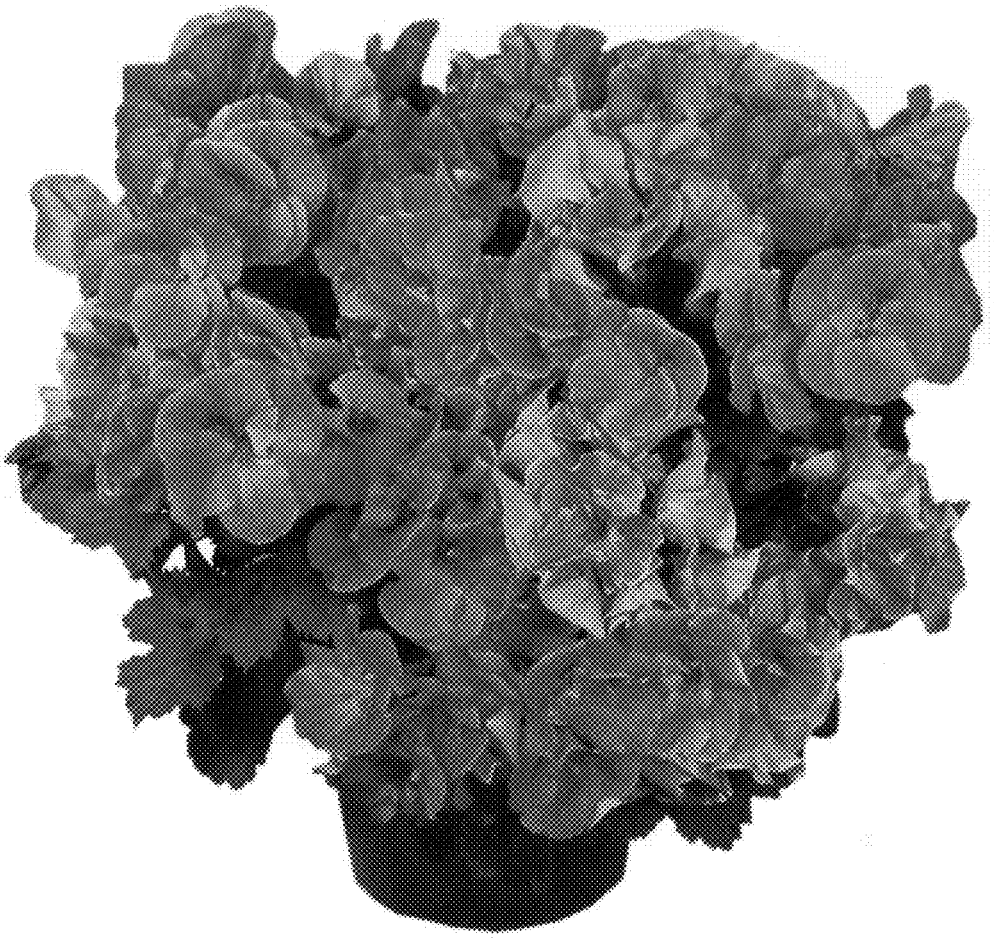

* * * * *